(12) United States Patent
Huemer

(10) Patent No.: US 7,948,619 B2
(45) Date of Patent: May 24, 2011

(54) CUVETTE AND METHOD FOR USING THE CUVETTE

(75) Inventor: Herfried Huemer, Feldbach (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 108 days.

(21) Appl. No.: 12/269,329

(22) Filed: Nov. 12, 2008

(65) Prior Publication Data

US 2009/0153851 A1 Jun. 18, 2009

Related U.S. Application Data

(60) Provisional application No. 60/987,448, filed on Nov. 13, 2007.

(51) Int. Cl.
*G01N 1/10* (2006.01)

(52) U.S. Cl. .................................................. 356/246

(58) Field of Classification Search .......... 356/244–246, 356/39–42, 432–444
See application file for complete search history.

(56) References Cited

U.S. PATENT DOCUMENTS

| | | |
|---|---|---|
| 3,972,614 A | 8/1976 | Johansen et al. |
| 5,757,482 A * | 5/1998 | Fuchs et al. ............... 356/246 |
| 6,579,722 B1 * | 6/2003 | Collins et al. ............... 436/172 |
| 7,531,786 B2 * | 5/2009 | Cunningham et al. ..... 250/214.1 |
| 2007/0064226 A1 | 3/2007 | Kolp et al. |

FOREIGN PATENT DOCUMENTS

| | | |
|---|---|---|
| DE | 10316723 A1 | 11/2004 |
| EP | 0433044 A1 | 6/1991 |
| EP | 1225439 A2 | 7/2002 |
| EP | 1406079 A2 | 4/2004 |
| EP | 1586888 A2 | 10/2005 |

OTHER PUBLICATIONS

International Search Report issued Mar. 12, 2009 in PCT Application No. PCT/EP2008/009514.

* cited by examiner

*Primary Examiner* — Michael P Stafira

(57) ABSTRACT

A cuvette with at least one sealing element and two transparent elements is provided where the latter are arranged at a distance from one another and define two opposing boundary faces of a sample channel and the sealing element defines side walls of the sample channel as a result of which the sample channel is formed as a channel that is closed in the longitudinal direction with an inlet opening and an outlet opening. At least one spacer is provided which keeps the transparent elements at a distance from one another. At least one of the two transparent elements has a projection which extends towards the other transparent element and forms a boundary surface of the sample channel such that the height of the sample channel is less than the height of the at least one spacer.

23 Claims, 5 Drawing Sheets

CUVETTE AND METHOD FOR USING THE CUVETTE

BACKGROUND OF THE INVENTION

The present invention relates to cuvettes and methods for using cuvettes. Oximetry modules are common components of medical-diagnostic analyzer systems and in particular of blood gas analyzers. Such blood gas analyzers are for example developed as portable analyzers for determining POC (point of care) parameters, for example the blood gases ($O_2$, $CO_2$, pH), the electrolytes (e.g., $K^+$, $Na^+$, $Ca^{++}$, $Cl^-$), the metabolites (e.g., glucose and lactate), the haematocrit, the haemoglobin parameters (e.g., tHb, $SO_2$, etc.), and bilirubin and are primarily used for the decentralized determination of the above-mentioned parameters in whole blood samples.

Ideally it should also be possible for "untrained" users to simply and intuitively operate such analyzers. Another important requirement for such an instrument is that it should be possible to operate it "virtually maintenance free" from the point of view of a user. "Virtually maintenance free" is generally understood to mean that also a (technically) untrained user only has to exchange consumables that are present in the form of cassettes and/or modules for the routine operation. It should be possible for the user to exchange all consumables by simple intuitive handling steps.

In systems such as those described in U.S. Pat. No. 3,972,614 the optical measuring chamber (cuvette) is designed as an integral component of the oximeter which remains permanently in the instrument. The analyzer described in U.S. Pat. No. 3,972,614 for the spectroscopic determination of parameters in blood samples such as, e.g., haemoglobin, also comprises means for the ultrasonic haemolysis of the blood sample, i.e., the destruction of the red blood corpuscles, in order to make the blood sample as free of scattering bodies as possible. Only by this means is it then possible to spectroscopically analyze the sample.

However, a disadvantage of the known system is the high risk of blockage during the planned period of use where in particular the fluidic coupling sites and the small pathlength of the sample channel are problematic. If dirtying or blockages occur in the cuvette area of these oximeter systems, they can often only be eliminated by a complicated exchange of the cuvette. This usually requires an appropriate training or a service technician has to be called thus frequently resulting in long unscheduled downtimes of the analyzer. Furthermore, the manual replacement of a cuvette in such systems often requires subsequent manual adjustment and calibration steps in order to again obtain reproducible measuring results.

A method and an instrument for the spectroscopic measurement of analytes in samples is known from the document EP 1586 888 A2. The instrument comprises a light source which generates a light path, a photodetector at the end of the light path and a slit opening in the light path into which a cuvette filled with the sample can be manually inserted. The cuvette is a simple plastic part which consists of a well provided with a handle for holding the sample and a cover which is joined to the well in a hinged fashion. This cuvette is a simple disposable product which is not suitable for carrying out a haemolysis and is also not intended to be used for this purpose. Rather it is described that the instrument is to be used for spectroscopic haemoglobin measurements as an indicator for haemolysis that has occurred in the sample. Another intended use of the known instrument is to monitor the decomposition or the reversal of decomposition of haemoglobin-based blood substitutes by measuring methaemoglobin. Due to its simple construction, the known cuvette is not dimensionally stable when pressure is applied and can therefore in no way be used in analytical systems in which it is mechanically pretensioned and/or stressed as is for example necessary for ultrasonic haemolysis. The lack of dimensional stability has a major effect on the result of spectroscopic measurements. Hence an accurate spectroscopic analysis of blood samples is not possible with this cuvette.

Therefore there is still a need for a cuvette which can be arranged in an exchangeable manner in a spectroscopic analyzer and is suitable for accurate analyses.

SUMMARY OF THE INVENTION

It is against the above background that the present invention provides certain unobvious advantages and advancements over the prior art. In particular, the inventors have recognized a need for improvements in cuvettes and methods for using cuvettes.

Although the present invention is not limited to specific advantages or functionality, it is noted that the present invention provides a cuvette which can be simply and intuitively replaced also by untrained users. The present invention also provides an easily exchangeable cuvette which, due to its design and the materials used, enables reliable determinations of haemoglobin derivatives and can also interact with an ultrasonic haemolysator of the analyzer in such a manner that a reliable haemolysis of a whole blood sample directly in the cuvette is possible.

Since in this case the cuvette is also a functional component of the haemolysing system, further requirements have to be met also with regard to the positioning and coupling of the cuvette in the analyzer. Thus, when a haemolysis by means of ultrasound is carried out in the cuvette, it is for example necessary to transfer the ultrasonic energy generated in the analyzer onto the cuvette in a well-defined manner. This can for example be achieved in that, after the reagent pack has been inserted in the analyzer, the cuvette is brought into a mechanically pretensioned state by means of a clamping mechanism which can be released again when the reagent pack is removed.

As a result of these additional requirements the cuvette combines a multitude of functionalities:

Exact definition of the height of the sample channel even under a mechanical load and in particular also when ultrasound is applied;
  Capable of docking to the additional fluidic system;
  Tolerance compensation;
  Optionally thermostatting the sample temperature;
  Fluidic leak tightness;
  Design of the sample channel as a haemolysis chamber;
  Defined mechanical and optical properties;
  Pressure tightness;
  Capable of being filled with blood without formation of any air bubbles and completely cleaned; and
  Gas tightness.

Depending on the requirements, all or also only some of these functionalities are relevant and have to be especially taken into account in the design of the cuvette.

The present invention also provides a cuvette with a sample channel having a height that is as small as possible but exactly defined so that, on the one hand, the sample analysis can be carried out using very small amounts of sample and, on the other hand, the effects of the strong absorption effect of blood on light in the visible wavelength range are reduced. The cuvette also exhibits excellent mechanical stability and dimensional stability despite the small height of the sample channel in order to generate sufficiently accurate results, but nevertheless is suitable for haemolysing the sample in the sample channel.

In accordance with one embodiment of the present invention, a cuvette is provided comprising at least one sealing element, two transparent elements, and at least one spacer. The two transparent elements are arranged at a distance from one another and define two opposing boundary faces of a sample channel and the at least one sealing element defines side walls of the sample channel such that the sample channel is closed in the longitudinal direction with an inlet opening and an outlet opening. The at least one spacer is configured to maintain the transparent elements at a distance from one another, and at least one of the transparent elements has a projection which extends towards the other transparent element and forms a boundary surface of the sample channel such that the height of the sample channel is less than the height of the at least one spacer.

The cuvette can be configured especially for use in spectroscopic analyzers and in particular for the spectroscopic determination of haemoglobin derivatives and quantities derived therefrom (oximetry and cooximetry), but is also suitable for analyzers whose operation is based on chemical measuring principles and for combined spectroscopic and chemical analyzers.

The invention additionally concerns a method for spectroscopically analyzing a sample using a cuvette.

Finally, the invention concerns a method for haemolysing a blood sample while using a cuvette.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1A:
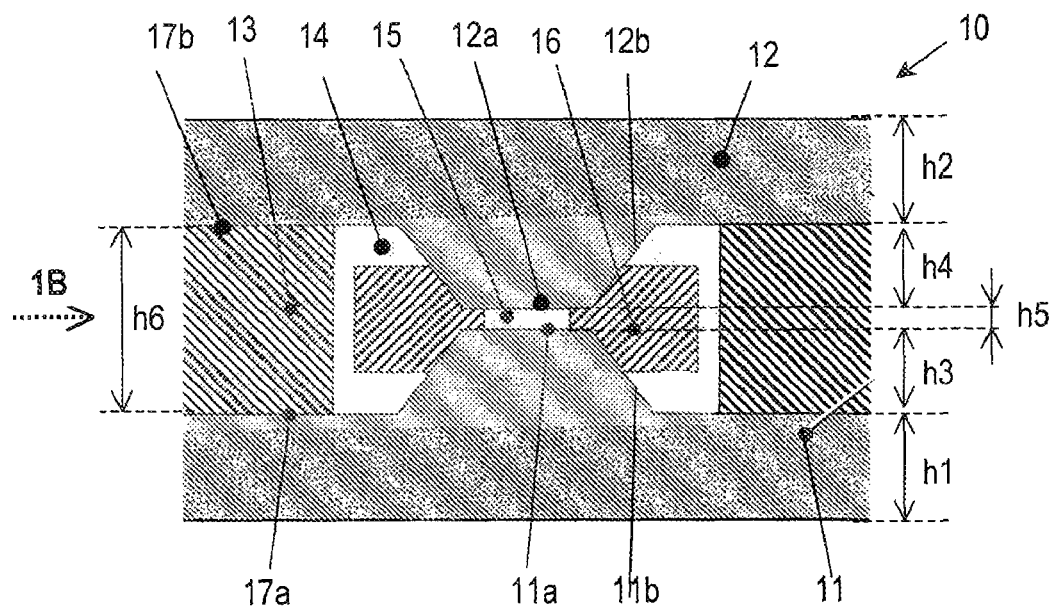
FIG. 1A and FIG. 1B show schematically a first embodiment of a cuvette according to the invention in cross-section and in a longitudinal section in the direction of the arrow 1B.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

The cuvette according to an embodiment of the invention comprises at least one sealing element and two transparent elements where the two transparent elements are arranged at a distance from one another and define two opposing boundary surfaces of a sample channel and the at least one sealing element defines side walls of the sample channel as a result of which the sample channel is formed as a channel that is closed in the longitudinal direction with an inlet opening and an outlet opening. At least one spacer is provided which keeps the transparent elements at a distance from one another and at least one of the two transparent elements has a projection which extends towards the other transparent element and forms a boundary surface of the sample channel so that the height of the sample channel is less than the height of the at least one spacer.

The provision of the projection on at least one of the two transparent elements allows a well-defined sample channel height to be achieved which is less than the height of the spacer, e.g., 0.1 or 1 mm in height. However, in this case the two transparent elements as well as the spacer are in the form of solid elements of sufficient thickness to have the preferred mechanical stability and dimensional stability and to be suitable for ultrasonic haemolysis.

In order that the spacer retains a satisfactory dimensional stability even in the case of ultrasonic applications, it is typical to manufacture it from an injection-mouldable plastic with high values for the modulus of elasticity (E module values) of typically more than 2500 MPa, and more typically of more than 5000 MPa.

In one embodiment of the cuvette according to the invention having a preferred mechanical strength and dimensional stability, the transparent elements are glued to the spacer by a dimensionally stable adhesive which typically has a defined layer thickness. Thus, an exact sample channel height can be set by adjusting the position of the transparent elements before the adhesive hardens.

In an alternative embodiment of the cuvette according to the invention the transparent elements are pressed or assembled with the spacer or joined to the spacer by means of clips. Also in this embodiment a high accuracy of shape is achieved when the individual parts have been machined so exactly before assembly that the required narrow fit tolerances are adhered to.

The sealing element in accordance with an embodiment of the present invention lies flat against the walls of the projections of the transparent elements. In order to prevent some of the sample from penetrating into small interspaces that may be present between the transparent elements and the sealing element due to the capillary effect at the interface, a further development of the invention provides that in the region of the inventive projection on at least one of the two transparent elements, the sealing element extends into the gap between the transparent elements. This is achieved by using a sealing element made of an elastic material which can have a Shore D hardness between about 50 and about 80, even more typically with a Shore D hardness between about 60 and about 70, and this sealing element is pressed against the transparent elements. Due to the yieldingness of the material of the sealing element it is pressed into the gap between the transparent elements and forms a sealing bead in the gap. The formation of the sealing bead can be assisted by providing a radius or a bevel on the edges of the transparent elements that face the gap. As a result one avoids so-called "sample carry-over" which is the contamination of a sample by remnants of earlier samples in the cuvette and the falsification of reference measurements. A particularly good sealing action and the avoidance of "sample carry-over" is achieved when the sealing element rests against a superficial surface of the projection of one or typically both transparent elements.

If a sealing element made of a light impermeable material is selected for the cuvette according to the invention or the sealing element is provided with a layer of a light impermeable material, the sealing element additionally forms an aperture for scattered light and extraneous light.

In one embodiment of the cuvette according to the invention the sealing element and the spacer form a combination element, e.g., a two-component injection-moulded part or a composite pressed part. Such a combination element considerably simplifies the assembly of the cuvette but nevertheless the preferred strength and tightness are achieved.

One embodiment of a cuvette according to the invention has transparent elements made of glass, typically pressed glass. This embodiment is distinguished by its good producibility and high dimensional stability.

According to the invention plastic having the following typical properties can be used as an alternative to glass: low strain birefringence, negligible creep behaviour, no/low gas permeability, chemical resistance, dimensional stability under heat, optical transparency in the visible (VIS) and near infrared (NIR) wavelength range. The visible range (VIS) is defined as the wavelength range between 380 and 780 nm; the near infrared range (NIR) is between 780 and 1400 nm. The transparent elements typically consist of plastics from the group of thermoplastic olefin polymers such as, for example, cycloolefin copolymers.

Selection of a material for the transparent elements from the materials listed above also allows the sample to be thermostatted in the cuvette. For example, blood samples have to be kept as accurately as possible at 37° C. during spectroscopic analysis because the spectra are temperature dependent.

In a further development of the cuvette according to the invention it is provided that the sample channel has an optical measuring area in which the transparent elements are in a plane-parallel arrangement. Adherence to plane parallelism has a direct effect on the measuring accuracy in absorption measurements. The exact plane parallelism achieved according to the invention thus contributes to increasing the accuracy of the spectroscopic analysis. Effects of scattered light, etc., are avoided when the optical measuring area is spaced apart from the edge of the sample channel.

In order to fill the sample channel with sample without bubbles, the sample channel is designed in a further embodiment of the cuvette according to the invention such that the width of the sample channel is reduced towards the inlet opening and towards the outlet opening and at the same time the height of the sample channel increases but the cross-sectional area of the sample channel typically remains essentially constant over its length. This embodiment leads to a sample channel with an essentially constant flow cross-section which prevents the formation of sample turbulence in the sample channel. Turbulence is avoided and a laminar flow is achieved by a design of the sample channel in which the sample channel only has continuous changes in the channel.

In order to build a small cuvette, the sample channel is curved in one embodiment of the cuvette according to the invention.

When the cuvette is integrated into a consumable of the spectroscopic analyzer, in particular into a so-called fluid pack which contains operating liquids required for the running operation of the analyzer such as calibration or reference liquids, wash or cleaning liquids or reagent liquids, and/or waste containers and which is regularly exchanged, the cuvette replacement becomes simple and intuitive even for an untrained user because it takes place in one operation together with the replacement of the consumable.

The present invention also concerns a method for spectroscopically analyzing a sample using a cuvette according to the invention. The analytical method comprises placing the sample in the cuvette and spectroscopically analyzing the sample in the cuvette.

Another aspect of the present invention provides a method for spectroscopically analyzing a blood sample using a cuvette according to the invention. The analytical method comprises placing the blood sample in the cuvette, haemolysing the blood sample in the cuvette and spectroscopically analyzing the haemolysed blood sample in the cuvette.

Figure 1B:
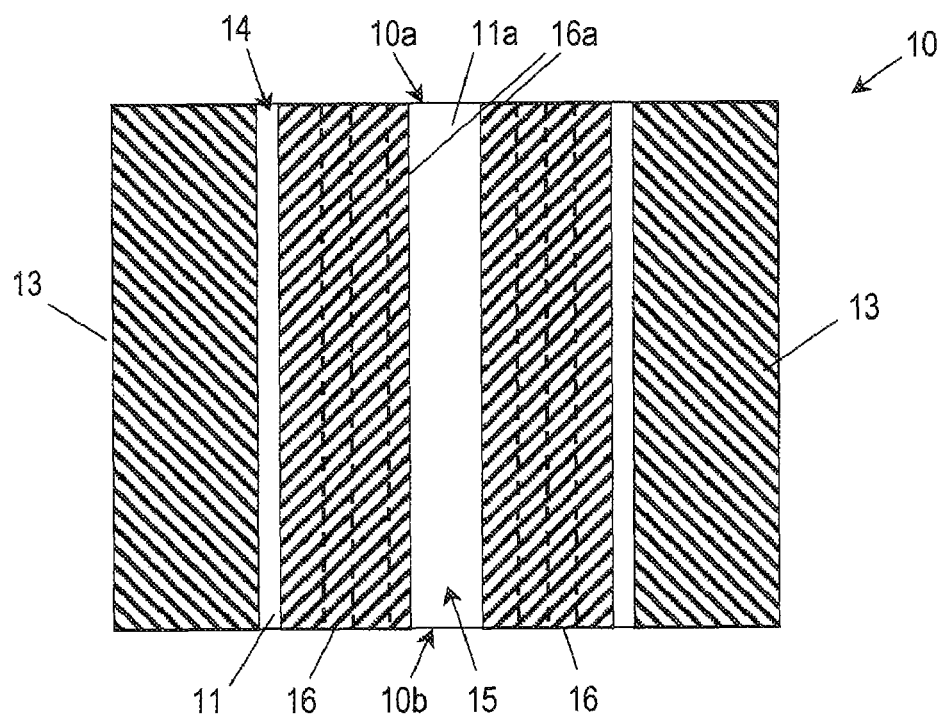

A first embodiment of a cuvette 10 according to the invention for a spectroscopic analyzer is now described on the basis of the schematic cross-sectional diagram of FIG. 1A and the longitudinal sectional diagram of FIG. 1B along the arrow 1B in FIG. 1A. The cuvette 10 comprises a spacer 13 which forms a recess 14. The spacer 13 has a height h6 and has plane-parallel upper and lower sides. In addition the cuvette 11 comprises a first and a second transparent element 11, 12 which have an essentially flat, plate-like base configuration with a height of h1 or h2. Each of the transparent elements 11, 12 has a projection 11a, 12a which projects from the plate-shaped base by a height h3, h4. In the present embodiment the projections 11a, 12a have a trapezoidal cross-section but the invention is not limited to such a cross-sectional shape. The base of the lower first transparent element 11 in the drawing rests flat against the underside of the spacer 13 and the projection 11a of the first transparent element extends into the recess 14 of the spacer 13. The base of the upper second transparent element 12 in the drawing rests flat against the upper side of the spacer 13 and the projection 12a of the second transparent element 12 likewise extends into the recess 14 of the spacer 13 and namely in such a manner that the two projections 11a, 12a face one another and are at a distance h5 from one another which results from the height h6 of the spacer minus the heights h3, h4 of the projections 11a, 12a, i.e., h5=h6−h3−h4. The two transparent elements 11, 12 are glued to the spacer 13 by dimensionally stable adhesive layers 17a, 17b where the adhesive is typically a UV hardening adhesive which is hardened by irradiating light through the transparent elements 11, 12.

The cuvette 10 also comprises a sealing element 16 which is located in the recess 14 of the spacer 13 between the projections 11a, 12a and rests against the side walls 11b, 12b of the projections 11a, 12a. Together with the sealing element 16, the faces of the projections 11a, 12a which face one another delimit a sample channel 15 which has a straight course in this embodiment. The opposite ends of the sample channel 15 end in an inlet opening 10a and an outlet opening 10b. The height of the sample channel 15 corresponds to the distance h5 between the facing end faces of the projections 11a, 12a and is thus considerably less than the height h6 of the spacer 13 and than the heights h1, h2 of the plate-shaped bases of the transparent elements 11, 12 and than the total height (h1+h3 and h2+h4) of the transparent elements 11, 12. This shows that the principle according to the invention allows relatively thick-walled elements to be used for the spacer 13 as well as for the transparent elements 11, 12 which due to their configuration and arrangement nevertheless result in a sample channel 15 with a very small height h5. It should be mentioned that in one variant of this first embodiment of the cuvette 10 according to the invention one of the two transparent elements 11, 12 could also be configured as a flat plate.

In order that the cuvette 10 has a suitable strength for ultrasonic applications, the spacer 13 can be manufactured from an injection-moldable plastic having high E-module values of typically more than about 2500 MPa and even more typically of more than about 5000 MPa.

The transparent elements 11, 12 can be made of glass, typically of pressed glass which can be easily machined. Alternatively they can be manufactured from a plastic which has the following properties: low strain birefringence, negligible creep behaviour, no/low gas permeability, chemical resistance, dimensional stability under heat, optical transparency in the visible (VIS) and near infrared (NIR) wavelength range. The transparent elements typically consist of plastics from the group of thermoplastic olefin polymers.

The sealing element 16 consists of an elastomer typically with a Shore D hardness between about 50 and about 80, even more typically with a Shore D hardness between about 60 and about 70. It lies flat against the side walls 11b, 12b of the projections 11a, 12a of the transparent elements 11, 12. In order to prevent part of the sample from penetrating into the interface between the side walls 11b, 12b and the sealing element 16 due to the capillary effect, the sealing element 16 can be pretensioned against the projections 11, 12 as a result of which a section 16a of the sealing element 16 is pressed into the gap between the facing end faces of the projections 11a, 12a and laterally seals this gap. This penetration of the section 16a into the gap between the facing end faces of the projections 11a, 12a is assisted by the slant of the side walls 11b, 12b which act as a chamfer. In order to prevent scattered light from forming at the side edges of the sample channel 15, a light-impermeable material can in addition be selected for the sealing element 16.

The cuvette 10 can be manufactured by firstly gluing the first transparent element 11 to the spacer 13 in such a manner that its projection 11a extends into the recess 14. Subsequently the sealing element 16 can be applied to the projection 11a as shown in FIGS. 1A and 1B. Afterwards the second transparent element 12 can be positioned on the spacer 13 in such a manner that its projection 12a is directed into the recess 14 and presses against the sealing element 16. As a result the sample channel 15 is formed. The height of the second transparent element 12 can be adjusted by a micrometer screw such that the sample channel has the predefined height h5. The spacing of the second transparent element 12 is typically adjusted by online measurement of the current distance between the end faces (inner boundary surfaces of the sample channel) of the projections 11a, 12a by means of a confocal microscope.

Subsequently, a UV-hardening adhesive can be introduced into the boundary layer between the spacer 13 and the second transparent element 12 and hardened by irradiation with UV light to obtain an adhesive layer 17b of an exactly defined thickness.

Figure 2A:
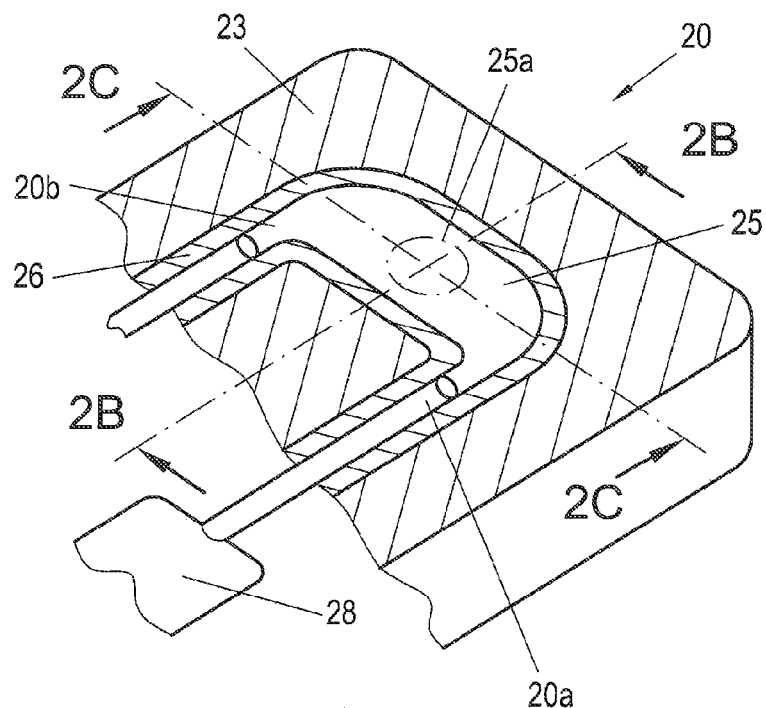
FIG. 2A, FIG. 2B and FIG. 2C show a second embodiment of a cuvette according to the invention in an isometric view, in a sectional view along the line 2B and in a sectional view along the line 2C of FIG. 2A.
Figure 2B:
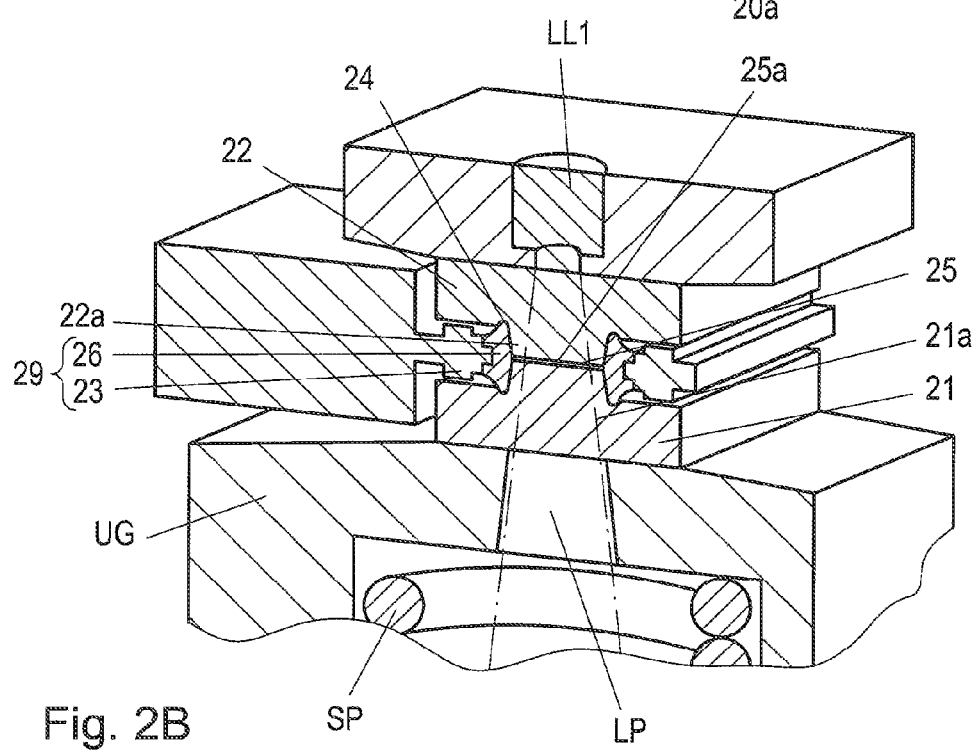

A second embodiment of a cuvette 20 according to the invention is elucidated on the basis of FIG. 2A and FIG. 2B. The cuvette 20 has a spacer 23, a first and a second transparent element 21, 22 and a sealing element 26. Each of the two transparent elements 21, 22 has a projection 21a, 22a and they are arranged opposite to one another on the spacer 23 such that the two projections 21a, 22a face one another and extend into a channel shaped recess 24. The distance between the end faces of the projections 21a, 22a corresponds to a defined height of a sample channel 25 formed between the end faces of the projections 21a, 22a. The periphery of the sample channel 25 is sealed by a sealing element 26 where the sealing element 26 rests against the outer surfaces of the projections 21a, 22a and pushes into the gap between them.

In contrast to the first embodiment, the sealing element 26 together with the spacer 23 is in the form of a combination element 29, e.g., a two-component injection-moulded part or a composite pressed part in the second embodiment of a cuvette 20 according to the invention. This has major advantages for the assembly of the cuvette 20. The materials of the spacer 23 and of the sealing element 26 can be as stated above. The sample channel 25 has an optical measuring area 25a in which the transparent elements 21, 22 are in a plane-parallel arrangement. In order to avoid edge effects the optical measuring area 25a is at a distance from the edge of the sample channel 25. A light guide LL1 ends near to the measuring area 25a and radiates light through the measuring area 25a along the light path LP which is analyzed spectroscopically after its passage through the measuring area 25. Reflective optical measuring systems are also envisaged as an alternative.

In the present embodiment of the invention, the sample channel 25 has a curved configuration so that the inlet opening 20a for the sample PB and the outlet opening 20b are on the same side which has the advantage of a reduced volume of the stricture and facilitates the replacement of the cuvette. In addition, it should be noted that the width of the sample channel 25 tapers from a central region which includes the measuring area 25a towards the inlet opening 20a and towards the outlet opening 20b, but at the same time the height of the sample channel 25 increases so that the cross-sectional area of the sample channel 25 remains essentially constant over its length. This prevents the formation of sample turbulence PB in the sample channel 25. For the same purpose the sample channel 25 only has continuous changes in the channel shape.

When assembling the cuvette 20, the two transparent elements 21, 22 can be glued to the spacer 23 as described above. Alternatively they can also be pressed or plugged in this embodiment.

The cuvette 20 can be specifically designed for a spectroscopic analysis of a blood sample as a sample PB in which the blood sample is haemolysed in the cuvette 20 before the spectroscopic analysis. For this purpose the cuvette 20 can be mechanically clamped into an ultrasonic generator UG (symbolized by the pretensioning spring SP). The ultrasonic generator UG generates ultrasonic energy and transfers it onto the transparent elements 21, 22 as a result of which haemolysis of the sample PB occurs in the sample channel 25.

Figure 2C:
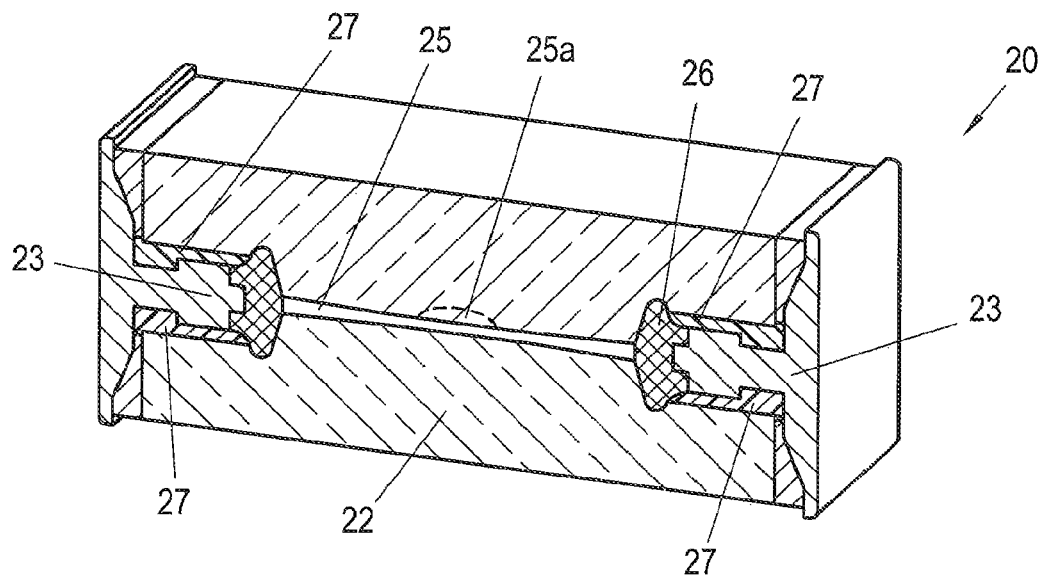

In one embodiment of the present invention best seen in FIG. 2C, which shows a longitudinal section through the sample channel 25, the sample channel 25 has inlet slopes which taper in a wedge-shaped manner towards the measuring area 25a and the faces of the transparent elements 21, 22 which define the sample channel have a plane-parallel course in the measuring area 25a. The adhesive layers 27 can also be seen in FIG. 2C which glue the spacer 23 to the two transparent elements 21, 22. The adhesive can be an adhesive which is dimensionally stable after hardening such that the adhesive layers 27 have a defined thickness.

Further variants of cuvettes according to the invention are elucidated in the following on the basis of the schematic cross-sectional diagrams of FIG. 3, FIG. 4 and FIG. 5. However, it is emphasized that the invention is not limited to the embodiment examples that are shown.

Figure 3:
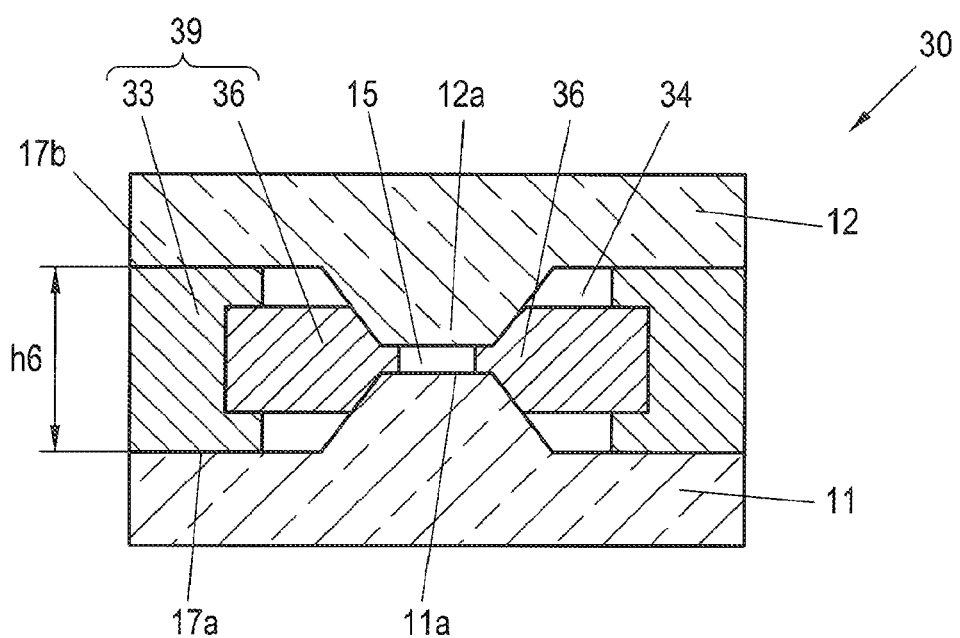
FIG. 3 shows schematically a third embodiment of a cuvette according to the invention in cross-section.

Firstly with reference to FIG. 3, this cuvette 30 has the same transparent elements 11, 12 as those of the cuvette 10 shown in FIG. 1 and described above. It is again mentioned that the first and the second transparent element 11, 12 have an essentially flat, plate-shaped based configuration and each has a trapezoidal projection 11a, 12a which projects from the plate-shaped base. The transparent elements 11, 12 are kept at a distance from one another by a spacer 33 where the spacer 33 has a height h6, plane-parallel upper- and undersides and defines a recess 34. The spacer 33 can, for example, be manufactured from an injection-moulded plastic having high E-module values of typically more than about 2500 MPa. The two transparent elements 11, 12 can be glued to the spacer 33 by means of dimensionally stable adhesive layers 17a, 17b. In addition the cuvette 30 can comprise a sealing element 36 which is located between the projections 11a, 12a in the recess 34 of the spacer 33 and rests against the side walls of the projections 11a, 12a. Together with the sealing element 36 the faces of the projections 11a, 12a that face one another define the sample channel 15. The sealing element 16 consists of an elastomer, typically with a Shore D hardness between about 50 and about 80, even more typically with a Shore D hardness between about 60 and about 70. In contrast to the embodiment of FIG. 1, the sealing element 36 together with the spacer 33 are in the form of a combination element 39 in the embodiment of FIG. 3. The spacer 33 and sealing element 36 can for example be joined to form the combination element 39 by gluing, assembling or by coextrusion.

Figure 4:
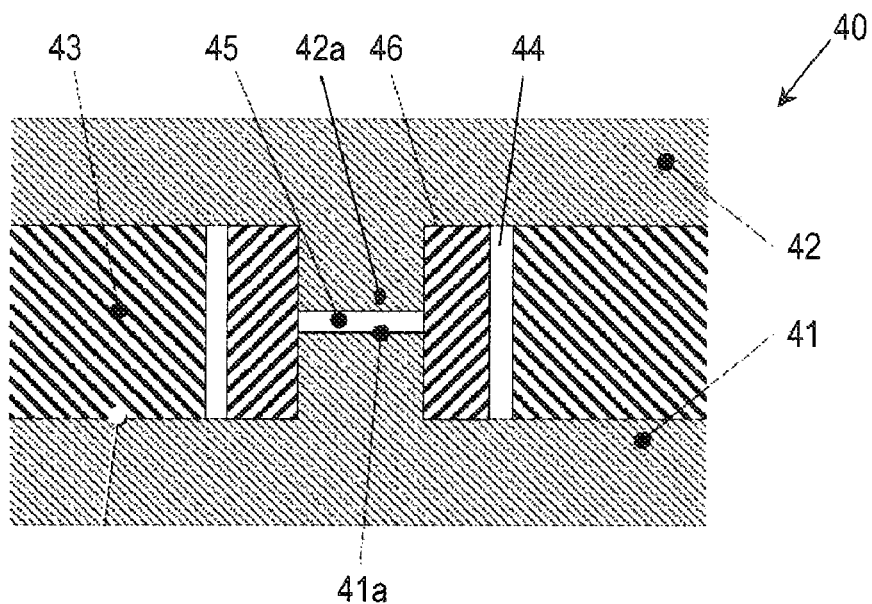
FIG. 4 shows schematically a fourth embodiment of a cuvette according to the invention in cross-section.

FIG. 4 shows a schematic cross-section of a further embodiment of a cuvette 40 according to the invention. This differs from the embodiments of FIGS. 1 and 3 in that it has a first and a second transparent element 41, 42 with an essentially flat, plate-shaped base configuration which, however, each has a projection 41a, 42a that is rectangular in cross-section and projects from the plate-shaped base. The transparent elements 41a, 42a are kept at a distance from one another by a spacer 43 as in the other embodiments. Furthermore, the cuvette 40 comprises a sealing element 46 which is arranged around the projections 41a, 42a in a recess 44 defined by the spacer 43 and rests against the side walls of the projections 41a, 42a. The faces of the projections 41a, 42a which face one another together with the sealing element 46 delimit a sample channel 45. The materials of the transparent elements 41, 42 and of the spacer 43 and of the sealing element 46 can be the same as those in the other embodiments.

Figure 5:
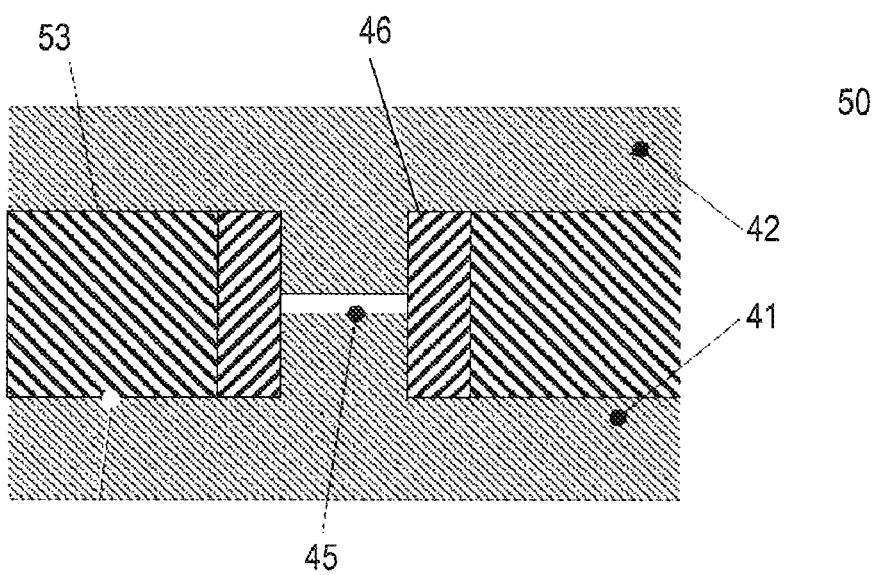
FIG. 5 shows schematically a fifth embodiment of a cuvette according to the invention in cross-section.

FIG. 5 shows a schematic cross-section of a further embodiment of a cuvette 50 according to the invention which only differs from the embodiment of FIG. 4 in that it has a spacer 53 which, compared with the spacer 43, defines a smaller recess that is completely occupied by the sealing element 46. The spacer 53 and the sealing element 46 can also be configured as a combination element.

Figure 6:
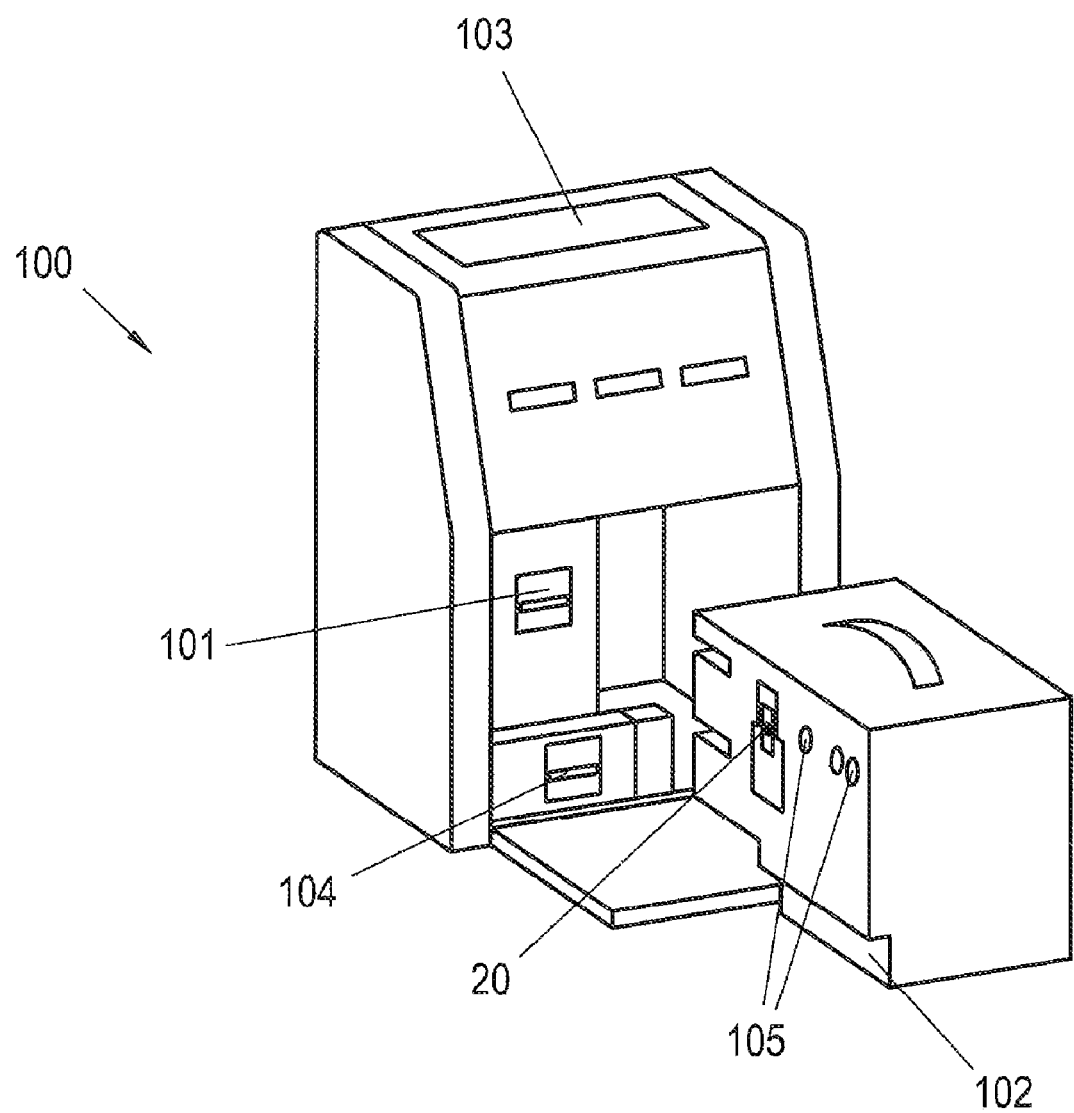
FIG. 6 shows schematically a modularly configured spectroscopic analyzer in which a cuvette according to the invention is used.

FIG. 6 shows schematically a modular concept of a spectroscopic analyzer 100 in which the cuvette 20 according to the invention is used that is described above on the basis of FIGS. 1 to 5. The analyzer 100 is designed to be "almost maintenance-free" so that all consumables required for routine operation are present in the form of cassettes and/or modules (so-called consumables) and can therefore also be replaced by (technically) untrained personnel. The consumable materials that are used are also encompassed by the term consumables in this embodiment in the following:

A sensor cassette 101 which contains at least some and typically all sensors required for the analyte determination.

A fluid pack 102 which contains the liquid container and waste container which contains the operating liquids required to run the analyzer 100 such as, for example, calibration or reference liquids, wash and cleaning liquids or reagent liquids. Further elements or functionalities such as the entire fluidic system or parts thereof, the sample input device or other sensory components can optionally also be contained in the fluid pack 102. According to the invention the fluidic pack 102 integrates a cuvette 20 according to the invention including the associated fluidic paths which supply and discharge liquids as described in more detail further below. This means that the cuvette 20 is routinely exchanged with each replacement of the fluidic pack 102 (e.g., at intervals of several weeks or after a certain number of measurements has elapsed).

A printer paper cassette 103 for an internal printer.

Optionally a quality control cassette 104 containing reference solutions in ampoules for carrying out an automated quality control which the personnel can exchange themselves by simple intuitive manual steps.

The subdivision of the consumables described here is only an example. It is also conceivable that (partial) functionalities or (partial) elements of several consumables are combined so that for example fewer or even only one consumable is required. On the other hand, it is also conceivable that (partial) functionalities or (partial) elements of individual consumables are divided among several (e.g., among several sensor cassettes or sensor modules). However, what is important is the basic idea of integrating the cuvette according to the invention into one of the consumables that is used so that it can be exchanged together with this consumable.

The consumables are coupled together or with the analyzer by compatible interfaces, e.g., in the form of fluidic docking nipples 105. The consumables can be manually connected to their respective counterparts by a simple manual sequence of movements carried out directly by the user, or by drives located in the device which automatically carry out the coupling after the user has only brought the cassette into "position".

In the present embodiment, the blood gas analyzer 100 contains an oximeter module in which the concentrations of the haemoglobin derivatives O2Hb, HHb, COHb, MetHb, as well as the blood parameters tHb (total haerhoglobin), SO2 (oxygen saturation) and bilirubin are determined by a spectrophotometric measuring method. Characteristic absorption properties of these substances are fused in this process and the measurements are evaluated by a mathematical algorithm. In order to achieve the required measuring accuracy, it is usually necessary to haemolyse the whole blood before the optical measurement. For this purpose the blood cells can for example be destroyed by means of ultrasonic energy in order to be able to carry out a measurement without interfering light scattering effects. Alternative haemolysis methods such as, for example, chemical haemolysis methods can also be used for this. The oximeter module comprises a lamp unit with (a) light source(s), fluidic supply and discharge leads, a haemolysator into which the cuvette 20 can be inserted and removed therefrom, a light guide which guides the light generated in the lamp unit to the cuvette 20 and a light guide which collects the light that has passed through the sample in the cuvette 20 and transmits it to a polychromator which spectrally separates the received light, and a detector for evaluating the spectral ranges of the received light.

The haemolysator is designed such that the cuvette 20 can be placed in the haemolysator as part of the consumable 102 when the consumable 102 is inserted into the analyzer 100 and is removed from the haemolysator when the consumable 102 is pulled out of the analyzer 100. This construction avoids the blockage problems of oximeter modules of known analyzers in which an optical measuring chamber (cuvette) is in the form of an integral component of the analyzer which remains permanently in the instrument.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A cuvette comprising:
   at least one sealing element;
   two transparent elements; and
   at least one spacer, wherein
      the two transparent elements are arranged at a distance from one another and define two opposing boundary faces of a sample channel,
      the at least one sealing element defines side walls of the sample channel such that the sample channel is closed in the longitudinal direction with an inlet opening and an outlet opening,
      the at least one spacer is configured to maintain the transparent elements at a distance from one another, and
      at least one of the transparent elements has a projection which extends towards the other transparent element and forms a boundary surface of the sample channel such that the height of the sample channel is less than the height of the at least one spacer.

2. The cuvette according to claim 1, wherein the spacer consists of an injection-moldable plastic having an E module value of more than about 2500 MPa.

3. The cuvette according to claim 2, wherein the injection-moldable plastic has an E module value of more than about 5000 MPa.

4. The cuvette according to claim 1, wherein the transparent elements are glued to the spacer by a dimensionally stable adhesive or are pressed with the spacer, plugged together with the spacer or joined to the spacer by clips.

5. The cuvette according to claim 1, wherein the sealing element projects into the gap between the transparent elements in the area of the projection on at least one of the two transparent elements.

6. The cuvette according to claim 1, wherein the sealing element rests against a lateral surface of the projection of one or both transparent elements.

7. The cuvette according to claim 1, wherein the sealing element consists of an elastic material.

8. The cuvette according to claim 7, wherein the elastic material has a Shore D hardness between about 50 and about 80.

9. The cuvette according to claim 8, wherein the elastic material has a Shore D hardness between about 60 and about 70.

10. The cuvette according to claim 1, wherein the sealing element consists of a light-impermeable material.

11. The cuvette according to claim 1, wherein the sealing element and the spacer form a combination element comprising a two-component injection-moulded part or a composite pressed part.

12. The cuvette according to claim 1, wherein the transparent elements are composed of glass elements or of plastics.

13. The cuvette according to claim 12, wherein the glass elements comprise pressed glass elements.

14. The cuvetter according to claim 12, wherein the plastic is a thermoplastic olefin polymer.

15. The cuvette according to claim 1, wherein the sample channel has an optical measuring area in which the transparent elements are in a plane-parallel arrangement.

16. The cuvette according to claim 15, wherein the optical measuring area is spaced apart from the edge of the sample channel.

17. The cuvette according to claim 1, wherein the width of the sample channel tapers towards the inlet opening and outlet opening and at the same time the height of the sample channel increases.

18. The cuvette according to claim 17, wherein the cross-sectional area of the sample channel remains essentially constant over its length.

19. The cuvette according to claim 1, wherein the cuvette is integrated into a consumable of the spectroscopic analyzer.

20. The cuvette according to claim 19, wherein the cuvette is integrated into a fluid pack which contains operating liquids and/or waste containers.

21. A method for spectroscopically analyzing a sample comprising:
   providing a cuvette according to claim 1;
   placing a sample in the cuvette; and
   analyzing the sample in the cuvette spectroscopically.

22. The method of claim 21, wherein the sample is blood.

23. The method of claim 22 further comprising haemolysing the blood sample.

* * * * *